United States Patent [19]

Solyom et al.

[11] Patent Number: 4,668,437

[45] Date of Patent: May 26, 1987

[54] NOVEL 20 BENZCYLAMINO PREGNENE DERIVATIVES AND PROCESS FOR PREPARING SAME

[75] Inventors: Sandor Solyom; Lajos Toldy; Katalin Szilagyi nee Farago, all of Budapest, Hungary

[73] Assignee: Richter Gedeon Vegyeszeti Gyar R.T., Budapest, Hungary

[21] Appl. No.: 775,347

[22] Filed: Sep. 11, 1985

[30] Foreign Application Priority Data

Sep. 12, 1984 [HU] Hungary .............................. 3435/84

[51] Int. Cl.[4] ................................................ C07J 00/00
[52] U.S. Cl. .............................. 260/397.4; 260/397.45; 260/397.47
[58] Field of Search ............ 260/397.4, 397.45, 397.47

[56] References Cited

U.S. PATENT DOCUMENTS 4,568,492 2/1986 Walker ...................... 260/239.55 R Primary Examiner—Leonard Schenkman
Assistant Examiner—Joseph A. Lipovsky
Attorney, Agent, or Firm—Keil & Weinkauf

[57] ABSTRACT

The invention relates to new pregnene derivatives of the general formula (I),

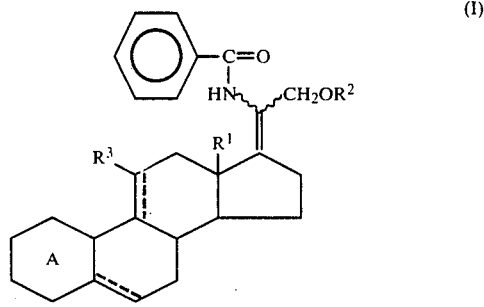

wherein
$R^1$ stands for a $C_{1-4}$ alkyl group;
$R^2$ stands for a hydrogen atom or a $C_{2-4}$ alkanoyl group;
$R^3$ stands for a hydrogen atom, a hydroxyl group or a $C_{2-4}$ alkanoyloxy group;
A represents a ring of the general formula (1)

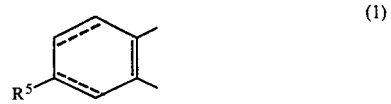

or a ring of the general formula (2),

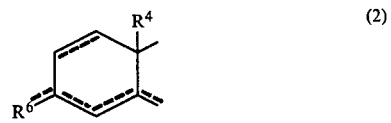

wherein
$R^4$ means a hydrogen atom or a methyl group;
$R^5$ stands for a hydroxyl group, a $C_{2-4}$ alkanoyloxy group or a $C_{1-3}$ alkoxy group;
$R^6$ means a hydroxyl group, a $C_{2-4}$ alkanoyloxy group, a $C_{1-3}$ alkoxy group, an oxo group or a $C_{2-3}$ alkylenedithio group;
the dotted line optionally represents one or more additional valence bonds, with the proviso that, when the dotted line between $C_9$ and $C_{11}$ represents an additional valence bond, then $R^3$ stands for a hydrogen atom; and the wavy line shows that the given substituent can be bound to the carbon atom in two alternative spatial arrangements, as well as to their stereoisomers and the mixture of these stereoisomers.

The compounds of the general formula (I) are valuable intermediates for the synthesis of known biologically active 21-hydroxyprogesterone derivatives.

4 Claims, No Drawings

NOVEL 20 BENZCYLAMINO PREGNENE DERIVATIVES AND PROCESS FOR PREPARING SAME

This invention relates to novel steroids, more particularly, to new pregnene derivatives of the general formula (I),

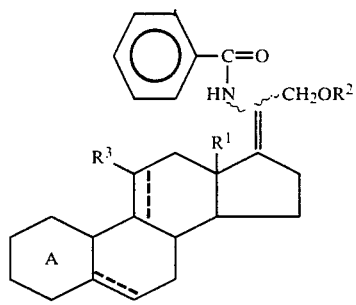

wherein
R[1] stands for a $C_{1-4}$ alkyl group;
R[2] stands for a hydrogen atom or a $C_{2-4}$ alkanoyl group;
R[3] stands for a hydrogen atom, a hydroxyl group or a $C_{2-4}$ alkanoyloxy group;
A represents a ring of the general formula (1)

or a ring of the general formula (2),

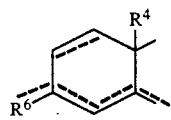

wherein
R[4] means a hydrogen atom or a methyl group;
R[5] means a hydroxyl group, a $C_{2-4}$ alkanoyloxy group or a $C_{1-3}$ alkoxy group;
R[6] means a hydroxyl group, a $C_{2-4}$ alkanoyloxy group, a $C_{1-3}$ alkoxy group, an oxo group or a $C_{2-3}$ alkylenedithio group;
the dotted line optionally represents one or more additional valence bonds, with the proviso that, when the dotted line between $C_9$ and $C_{11}$ represents an additional valence bond, then R[3] stands for a hydrogen atom; and the wavy line shows that the given substituent can be bound to the carbon atom in two alternative spatial arrangements,
as well as to their stereoisomers and the mixture of these stereoisomers.

The compounds of the general formula (I) (the compounds of the invention) are valuable intermediates, e.g. for the synthesis of known biologically active 21-hydroxyprogesterone derivatives (such as deoxycorticosterone and its acetate) as well as of corticosteroids containing a dihydroxyacetone side chain at $C_{17}$.

The building-up of the $C_{17}$ substituent, which is characteristic of pregnanes and corticosteroids, may among others be achieved through compounds obtained by the condensation reaction of 17-ketosteroids with an appropriate reactant as well as by the further transformation of the thus-obtained compounds.

Tere are several processes utilizing this principle, which are known from the literature.

G. Neef et al. [Chem. Ber. 113, 1184 (1980)] described the condensation of 17-ketosteroids with methoxyacetic ester. G. Haffer et al. [Chem. Ber. 111, 1533 (1978)] published the condensation of 17-ketosteroids with cyanoacetic ester; and the condensation of 17-ketosteroids with an isocyanoacetic ester was reported by two various teams [U. Schöllkopf and K. Hantke: Chem. Ber. 109, 3964 (1976); L. Nedelec et al.: J. Chem. Soc. Chem. Commun. 1981, 775].

Pregnane intermediates can also be obtained by condensing 17-ketosteroids with ethyl trichloroacetate or methoxydichloroacetate, respectively [A. R. Daniewski, and W. Wojciechowska: J. Org. Chem. 47, 2993 (1982); idem: Synthesis 1984, 132].

D. H. R. Barton et al. [J. Chem. Soc. Chem. Commun. 1981, 774] reported on the condensation of 17-ketosteroids with diethyl α-isocyanoethyl phosphonate as well as the further transformation of the 17(20)-pregnene derivatives obtained. The same authors described a pregnane synthesis based on an intermediate obtained by the condensation of dehydroepiandrosterone with nitromethane [J. Chem. Soc. Chem. Commun. 1982, 551].

It is a common characteristic feature of the methods reported hitherto that the condensation should be carried out in the presence of a base (or, in the case of dichloro- and trichloroacetate esters, by using diethylaluminium chloride together with zinc).

Surprisingly, now it has been found that 17-ketosteroids can be condensed with 2-phenyl-2-oxazoline-5-one of the formula (III)

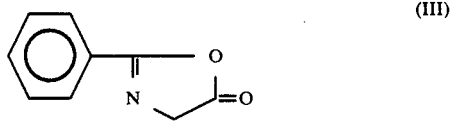

to give the new azlactone derivatives of the general formula (IV),

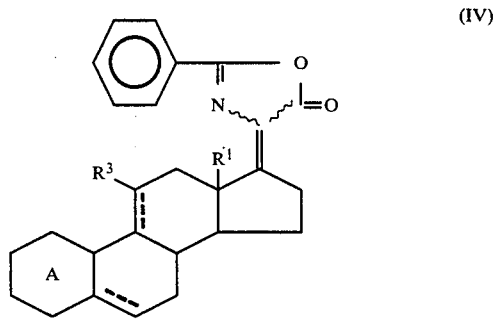

wherein R[1] and R[3] have the same meaning as above, in good yields, when the reaction is carried out in the presence of titanium tetrachloride and the thus-obtained complex is decomposed by adding pyridine. Such a type of conversions of 17-ketosteroids has not been known hitherto.

The azlactone ring of the derivatives of the general formula (IV) can be opened (cleaved) with an alkali metal lower alkoxide to give the new alkyl 20-acylamino-pregn-17-ene-21-oate esters of the general formula (V)

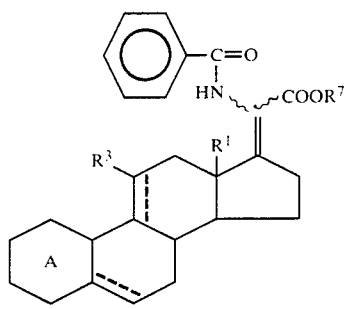

in nearly quantitative yields. After reducing the ester group and optionally after acylating, the compounds of the general formula (I) are obtained in good yields.

Based on these facts, according to an other aspect of the invention, there is provided a process for the preparation of the new pregnene derivatives of the general formula (I), wherein $R^1$, $R^2$, $R^3$, ring A and therein $R^4$, $R^5$ and $R^6$ as well as the meaning of the dotted and wavy lines are as defined above, and their stereoisomers as well as the mixture of these stereoisomers, which comprises (a) reducing an alkyl 20-acylamino-pregn-17-ene-21-oate of the general formula (V), wherein $R^1$, $R^3$, ring A and therein $R^4$, $R^5$ and $R^6$ as well as the meaning of the dotted and wavy lines are as defined above, and $R^7$ stands for a $C_{1-3}$ alkyl group, with a complex aluminium hydride, or (b) reacting a 17-(phenyloxazoline-4'-ylidene)-androstene derivative of the general formula (IV), wherein $R^1$, $R^3$, ring A and therein $R^4$, $R^5$ and $R^6$ as well as the meaning of the dotted and wavy lines are as defined above, with an alkali metal $C_{1-3}$ alkoxide and reducing the thus-obtained compound of the general formula (V), wherein $R^1$, ring A and therein $R^4$, $R^5$ and $R^6$ as well as the meaning of the dotted and wavy lines are as defined above, $R^3$ stands for a hydrogen atom or a hydroxyl group and $R^7$ represents a $C_{1-3}$ alkyl group, with a complex aluminium hydride, or (c) reacting a 17-ketosteroid derivative of the general formula (II),

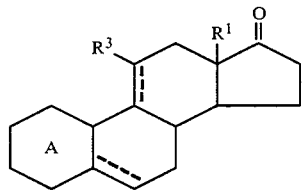

wherein $R^1$, $R^3$, ring A and therein $R^4$, $R^5$ and $R^6$ as well as the meaning of the dotted lines are as defined above, with an azlactone derivative of the formula (III) in the presence of titanium tetrachloride, treating the reaction mixture with an organic base, then reacting the thus-obtained 17-(phenyloxazoline-4'-ylidene)-androstene derivative of the general formula (IV), wherein $R^1$, $R^3$, ring A and therein $R^4$, $R^5$ and $R^6$ as well as the meaning of the dotted and wavy lines are as defined above, with an alkali metal $C_{1-3}$ alkoxide, and reducing the thus-formed compound of the general formula (V), wherein $R^1$, ring A and therein $R^4$, $R^5$ and $R^6$ as well as the meaning of the dotted and wavy lines are as defined above, $R^3$ stands for a hydrogen atom or a hydroxyl group, and $R^7$ represents a $C_{1-3}$ alkyl group, with a complex aluminium hydride, then optionally acylating the compound of the general formula (I) obtained by any one of the processes (a) or (b) or (c), wherein $R^1$, $R^3$, ring A and therein $R^4$, $R^5$ and $R^6$ as well as the meaning of the dotted and wavy lines are as defined above, and $R^2$ stands for a hydrogen atom, with an activated derivative of a $C_{2-4}$ alkanecarboxylic acid and/or converting the alkylenedithio group of a compound of the general formula (I) obtained as described above, wherein $R^1$, $R^2$, $R^3$ are as defined above, ring A represents a group of the general formula (2), $R^4$ and the meaning of the dotted and wavy lines are as defined above, and $R^6$ stands for a $C_{2-3}$ alkylenedithio group, to an oxo group in a manner known in the art by hydrolysis or by oxidative or alkylating hydrolysis and/or, if desired, separating the structural isomers of a compound of the general formula (I) obtained as described above.

According to a preferred embodiment of the process of the invention, 2-phenyl-2-oxazoline-5-one, which can be prepared by dehydratating hippuric acid [M. Crawford and W. T. Little; J. Chem. Soc. 1959, 729] is condensed with 17-ketosteroids in the presence of titanium tetrachloride as a condensating agent. This condensation is preferably performed by adding dropwise a solution containing the ketosteroid and an excess (e.g. 5 to 50%) of 2-phenyl-2-oxazoline-5-one in tetrahydrofuran to a solution containing 1 to 30 equivalents, preferably 3 to 12 equivalents, of titanium tetrachloride in carbon tetrachloride, then adding dropwise an organic base, preferably pyridine in an amount equivalent to or of a little excess over the amount of the titanium tetrachloride used. After the completion of the reaction, the mixture is decomposed by adding water or an aqueous sodium chloride solution and the product is isolated by extraction. The thus-obtained 17-oxazolin-ylidene-steroids of the general formula (IV) are isolated as a mixture of their geometrical isomers (Z/E). These isomers may be separated by using chromatography or recrystallization methods but this is not required to carry out the next step of the synthesis.

In the following step of the process of the invention, the azlactone ring of the compounds of the general formula (IV) is cleaved (opened) by an alkali metal lower alkoxide to give alkyl pregnene-21-oate esters of the general formula (V). Preferably, this reaction is achieved by using sodium methoxide in methanol as solvent. Sodium methoxide is usually employed in an excess, though this reaction also proceeds on the effect of sodium methoxide taken in an amount lower than one equivalent. The compounds of the general formula (V) are in general formed in quantitative yields. It is obvious that, on using a compound of the general formula (IV) as a mixture of isomers, the compound of the general formula (V) is also obtained as a mixture of the Z/E isomers; while on cleaving the azlactone ring of an individual pure stereoisomer, the corresponding sterically uniform compound of the general formula (V) is obtained.

The carboalkoxy group in the compounds of the general formula (V) can be reduced by using a complex aluminium hydride, e.g. lithium aluminium hydride, diisobutylaluminium hydride or sodium bis(methoxy-ethoxy)aluminium hydride. This reduction can preferably be achieved by using the last reducing agent in an amount of 2 to 10 equivalents e.g. in toluene as solvent and carrying out the reduction in an inert solvent, e.g. tetrahydrofuran. After completion of the reaction, the excess of the reducing agent is decomposed by adding a lower aliphatic alcohol, and after dilution with water the product is isolated by extraction.

On reducing a stereoisomeric mixture of the compound of the general formula (V), the compound of the general formula (I) will also be obtained as a mixture of the Z/E isomers; while on reducing an individual, pure stereoisomer, a sterically uniform compound of the general formula (I) will be produced.

The isomeric mixture obtained on the reduction can optionally be separated by using chromatography and/or recrystallization.

The 11- and 21-hydroxyl group of the compounds of the general formula (I) prepared by using the process of the invention may optionally be acylated in a manner known in the art; the 3-thioketal substituent may also be hydrolyzed in a manner known from the literature [see, e.g. B. T. Gröbel and D. Seebach: Synthesis 1977, 357]. These conversions also represent a part of the process of the invention.

The starting materials of the general formula (II) used in the process of the invention, e.g. dehydroepiandrosterone acetate, 1,4-androstadiene-3,17-dione, 11β-hydroxy-4-androstene-3,17-dione or estrone-3-methyl ether are known and commercially available. The various unknown androstenedione-3-ethylenedithioacetal derivatives can similarly be prepared in known ways as described in the literature [J. R. Williams and G. M. Sarkisian: Synthesis, 1974, 32] for known analogues.

The starting material of the formula III, 2-phenyl-2-oxazolin-5-one is also known [J. Chem. Soc. 1959, 729].

The invention is illustrated in detail by the aid of the following non-limiting Examples. [The important $^1$H-NMR data are given as δppm units; the $R_f$ values are given for a silica gel layer of 0.2 mm in thickness (Kieselgel 60, Merck); the spots were detected by spraying with sulphuric acid and heating at 110° C.]

EXAMPLE 1

Preparation of
20-benzoylamino-5,17-pregnadiene-3β,21-diol

Step (a)

Preparation of
17-(2'-phenyl-5'-oxo-2'-oxazoline-4'-ylidene)-5-androstene-3β-ol acetate A solution of 6.6 ml (60 mmoles) of titanium tetrachloride in 13 ml of carbon tetrachloride is dropped to 40 ml of dry tetrahydrofuran at 0° to 5° C. while stirring during 30 minutes. Then, 6.6 g (20 mmoles) of dehydroepiandrosterone acetate and 3.54 g (22 mmoles) of 2-phenyl-2-oxazoline-5-one dissolved in 40 ml of tetrahydrofuran are dropped in during about 20 minutes and after stirring for 10 minutes, 10 ml of pyridine are added dropwise during 90 to 120 minutes. Then the mixture is allowed to warm to room temperature and after 2 hours it is decomposed by adding 100 ml of an ice-cold 10% sodium chloride solution. The product is extracted three times with 60 ml of dichloromethane each, the organic solution is washed to neutral with water, dried and evaporated. The crystalline residue (9.9 g) is washed with diisopropyl ether to give 7.8 g (82% yield) of the aimed product as a mixture of the Z and E isomers, m.p.: 182°–185° C.

IR (KBr): 1790 cm$^{-1}$ (CO, ring), 1730 cm$^{-1}$ (CO, acetate), 1660 (C=N).

$^1$H-NMR (CDCl$_3$): 106 (s, 6H, H-18,19); 2.03 (s, 3H, Ac); 4.60 (m, 1H, H-3); 5.40 (m, 1H, H-6).

Step (b)

Preparation of methyl
3β-hydroxy-20-benzoylamino-5,17-pregnadiene-21-oate 12.44 g (26.3 mmoles) of 17-(2'-phenyl-5'-oxo-2'-oxazoline-4'-ylidene)-5-androstene-3β-ol acetate [prepared as described in Step (a)] are added portionwise under stirring to a solution prepared from 1.2 g of sodium in 160 ml of methanol. The transitory suspension is being dissolved within a few minutes. After stirring at room temperature for 40 minutes, the mixture is poured into 400 ml of ice-cold water, the precipitate is filtered and washed to neutral with water. After drying 12.0 g (98% yield) of the aimed product are obtained as a mixture of the Z and E isomers, m.p. 138°–140° C. The isomers can be separated on a silica gel column by using a 3:1 mixture of chloroform and ethyl acetate as eluant to give the E isomer with an $R_f$ value of 0.49, m.p.: 140°–141° C. and the Z isomer with an $R_f$ value of 0.35, m.p.: 246°–247° C.

IR (KBr): 3460 and 3380 cm$^{-1}$ (OH, NH), 1705 cm$^{-1}$ (CO), 1650 cm$^-$(amide I).

Z isomer: $^1$H-NMR (CDCl$_3$): 0.95 (s, 6H, H-18, 19); 3.63 (s, 3H, OCH$_3$); 5.30 (m, 1H, H-6); 7.2 (b, 1H, NH).

E isomer: $^1$H-NMR (CDCl$_3$): 1.00 (s, 3H, H-18); 1.10 (s, 3H, H-19); 3.4 (m, 1H, H-3); 3.73 (s, 3H, OCH$_3$); 5.30 (m, 1H, H-6); 7.2 (b, 1H, NH).

Step (c)

Preparation of
20-benzoylamino-5,17-pregnadiene-3β,21-diol 33.5 g (116 mmoles) of sodium bis(methoxy-ethoxy)aluminium hydride as a 70% toluene solution are diluted with 75 ml of toluene and the obtained solution is dropped to a solution containing 5.97 g (12.8 mmoles) of methyl 3β-hydroxy-20-benzoylamino-5,17-pregnadiene-21-oate [prepared as described in Step (b)] in 100 ml of dry tetrahydrofuran while stirring under nitrogen at −10° C. The precipitate arising at the start of the reaction is later dissolved. The reaction mixture is stirred at −5° C. for additional 1 hour, then the excess of the reducing agent is decomposed by adding dropwise 24 ml of ethanol. The mixture is evaporated to its one-third volume and the residue is taken up in 300 ml of 20% aqueous potassium sodium tartrate solution. The product is extracted four times with 100 ml of ethyl acetate each, the organic phase is washed to neutral with a 10% aqueous sodium chloride solution, then dried and evaporated. After washing the crystalline residue on the filter with 5 ml of diisopropyl ether, 5.0 g (89% yield) of the aimed product are obtained as a mixture of the Z/E isomers, m.p: 183°–185° C.

IR (KBr): 3200–3500 cm$^{-1}$ (OH+NH), 1640 cm$^{-1}$ (amide I).

$^1$H-NMR (CDCl$_3$+DMSO-d$_6$): 0.76 (s, 3H, H-18); 1.00 (s, 3H, H-19); 5.30 (m, 1H, H-6).

The product of this Example can be converted in the following way to 5-pregnene-3β,21-diol-20-one or 5-pregnene-3β,21-diol-20-one-3,21-diacetate, respectively, which are known intermediates for building up the corticoidal side chain [Helv. Chim. Acta 39, 359 (1951)].

Step (1)

Preparation of 5-pregnene-3β,21-diol-20-one 21-benzoate

A suspension containing 8.75 g (20 mmoles) of 20-benzoylamino-5,17-pregnadiene-2β,21-diol in 175 ml of 90% acetic acid is refluxed for 2 hours to give a clear solution. After cooling down, the solution is poured into 2 liters of ice-cold 10% sodium chloride solution. The precipitate is filtered, washed to neutral with water and dried to give 9.11 g of a crude product which is a mixture of the aimed product with 5-pregnene-3β,21-diol-20-one 3-acetate 21-benzoate.

This crude product is subjected to chromatography on a silica gel column by using a 8:1:1 mixture of benzene/ethyl acetate/acetone as eluant. 5-Pregnene-3β,21-diol-20-one 3-acetate 21-benzoate is contained in the fractions with an $R_f$ value of about 0.9, the evaporation of which gives 3.08 g (34% yield) of a crystalline product, m.p.: 161°–162° C.

On evaporation of the fractions with an $R_f$ value of about 0.5, 5.34 g (58% yield) of the aimed crystalline product are obtained, m.p.: 180°–181° C., $[\alpha]_D = +55.9°$ (c=0.5 in chloroform).

Step (2)

Preparation of 5-pregnene-3β,21-diol-20-one 15 g of potassium hydrogen carbonate dissolved in 28 ml of water are added to a suspension containing 5 g of the crude product (containing the above-mentioned two components)(prepared as described above) in 200 ml of methanol. The mixture is refluxed for 3 hours, then the solvent is evaporated. The residue is taken up in 300 ml of water and extracted three times with 150 ml of dichloromethane each. The organic phase is washed twice with 100 ml of a saturated sodium chloride solution each, dried and evaporated. The residue is subjected to chromatography on a silica gel column by using an 8:1:1 mixture of benzene/ethyl acetate/acetone as eluant to give 2.24 g of the aimed product in crystalline form, m.p.: 174°–176° C., $[\alpha]_D = +9.0°$ (c=1.0 in chloroform).

Step (3)

Preparation of 5-pregnene-3β,21-diol-20-one 3,21-diacetate

A solution containing 1 g (3 mmoles) of 5-pregnene-3β,21-diol-20-one [prepared as described in Step (2)] in 10 ml of acetic acid and 2 ml acetic acid anhydride is stirred with 0.1 g of p-toluenesulphonic acid at room remperature for 5 hours. Then the mixture is poured into 100 ml of ice-water, the precipitate is filtered, washed to neutral with water and dried to give 1.24 g (99% yield) of the aimed product, m.p.: 167°–168° C. (after recrystallization from methanol), $[\alpha]_D = +24.1°$ (c=0.5 in chloroform).

EXAMPLE 2

Preparation of 20-benzoylamino-5,17-pregnadiene-3β,21-diol diacetate 3.5 g of 20-benzoylamino-5,17-pregnadiene-3β,21-diol [prepared as described in Example 1, Step (c)] are dissolved in a mixture of 35 ml of benzene, 14 ml of pyridine and 8 ml of acetic acid anhydride. The solution is heated at 60° C. for 24 hours, then diluted with 50 ml of benzene, washed successively with 10% sodium chloride solution, then with saturated aqueous sodium hydrogen carbonate solution and again with sodium chloride solution, then dried and evaporated to dryness. To the residue 20 ml of methanol are added and evaporated. The crystalline residue is treated with diisopropyl ether and filtered to give 4.2 g (100% yield) of the aimed product, m.p.: 148°–150° C.

EXAMPLE 3

Preparation of 20-benzoylamino-21-hydroxy-4,17-pregnadiene-3-one ethylenedithioacetal

Step (a)

Preparation of 17-(2'-phenyl-5'-oxo-2'-oxazoline-4'-ylidene)-4-androstene-3-one ethylenedithioacetal A solution containing 13.6 ml (123 mmoles) of titanium tetrachloride in 25 ml of carbon tetrachloride is dropped to 60 ml of tetrahydrofuran at 0°–5° C. during 30 minutes. Subsequently, a solution containing 7.47 g (20.6 mmoles) of 4-androstene-3,17-dione-3-ethylenedithioacetal [J. R. Williams and G. M. Sarkisian: Synthesis, 1974, 32] and 3.7 g (23 mmoles) of 2-phenyl-2-oxazoline-5-one in 40 ml of tetrahydrofuran is dropped to the mixture at the same temperature, and after 15 minutes 20 ml of pyridine are added dropwise during 2 hours. The reaction mixture is then allowed to warm to room temperature and decomposed after 2 hours by adding 200 ml of ice-cold sodium chloride solution. The product is extracted three times with 100 ml of dichloromethanne each, the organic solution is washed to neutral with sodium chloride solution, dried and evaporated. The oily residue is subjected to chromatography on a column containing 600 g of silica gel by using a 96:4 mixture of benzene and acetone as eluant. Before applying onto the column, a part of the product (2.22 g, m.p.: 266°–267° C.) crystallizes out. This product is the major part of the geometrical isomer which is more apolar in the given system.

The mixture of the isomers is taken off as a single fraction from the column. On evaporation, 4.87 g of the aimed product are obtained, m.p.: 217°–219° C. The total yield is 68%.

IR (KBr): 1785 cm$^{-1}$ (CO, ring), 1650 cm$^{-1}$ (C=N).
$^1$H-NMR (CDCl$_3$): 1.05 (s, 6H, H-18, 19); 3.3 (m, 4H, SCH$_2$), 5.42 (3, 1H, H-4).

Step (b)

Preparation of methyl 20-benzoylamino-4,17-pregnadien-3-one ethylene-dithioacetal-21-oate 7.10 g (14 mmoles) of 17-(2'-phenyl-5'-oxo-2'-oxazoline-4'-ylidene)-4-androstene-3-one-ethylenedithioacetal [prepared as described in Step (a) above] are added portionwise while stirring to a solution prepared from 0.39 g of sodium and 50 ml of methanol at room temperature. To the suspension obtained, 40 ml of tetrahydrofuran are added. During the reaction a solution is obtained. After 90 minutes, the reaction mixture is poured into 1800 ml of water and the crystalline precipitate is filtered. The wet product is dissolved in ethyl acetate, washed to neutral with water, the solution is dried over anydrous magnesium sulphate and evaporated to give 7.56 g (93% yield) of a foamy product which becomes crystalline on treating with diisopropyl ether, m.p.: 144°–146° C. a mixture of the Z and E isomers.

IR (KBr): 3420 cm$^{-1}$ (NH); 1720 cm$^{-1}$ (CO), 1660 cm$^{-1}$ (amide I).

$^1$H-NMR(CDCl$_3$): 0.96+1.03+1.10 (3x s, 6H, H-18, 19); 3.72+3.65 (2x s, 3H, OCH$_3$); 5.45 (s, 1H, H-4); 7.2 (b, 1H, NH).

Step (c)

Preparation of 20-benzoylamino-21-hydroxy-4,17-pregnadiene-3-one-ethylenedithioacetal 2.66 g (4.9 mmoles) of methyl 20-benzoylamino-4,17-pregnadiene-3-one-ethylenedithioacetal-21-oate [prepared as described in Step (b) above] are reduced as described in Example 1, Step (c). The reaction mixture is worked up in the same way to give 2.52 g (100% yield) of the aimed oily product. The isomers are separated by chromatography on a silica gel column by using a 3:1 mixture of chloroform and ethyl acetate as eluant. After recrystallization from ethyl acetate, the isomer with the R$_f$ value of about 0.6 (0.87 g yield) melts at 220°–222° C.

IR (KBr): 3440 cm$^{-1}$ (OH), 3250 cm$^{-1}$ (NH), 1650 cm$^{-1}$ (amide I).

$^1$H-NMR (DMSO-d$_6$): 0.97 (s, 3H, H-18); 1.01 (s, 3H, H-19); 4.15 (s, 2H, OCH$_2$), 5.40 (s, 1H, H-4).

After recrystallization from ethyl acetate, the other isomer with an R$_f$ value of 0.3 (0.80 g yield) melts at 197°–198.5° C.

IR (KBr): 3330 cm$^{-1}$ (OH); 3150 cm$^{-1}$ (NH), 1640 cm$^{-1}$ (amide I).

$^1$H-NMR (CDCl$_3$): 0.93 (s, 3H, H-18); 1.00 (s, 3H, H-19); 4.15 (s, 2H, OCH$_2$); 5.45 (s, 1H, H-4).

EXAMPLE 4

Preparation of 20-benzoylamino-21-hydroxy-4,17-pregnadiene-3-one-ethylenedithioacetal 5.46 g (10.8 mmoles) of 17-(2'-phenyl-5'-oxo-2'-oxazolin-4'-ylidene)-4-adrostene-3-one-ethylenedithioacetal [prepared as described in Example 3, Step (a)] are reacted with sodium methoxide as described in Example 3, Step (b). The crude product is dissolved in 200 ml of benzene, washed with water to neutral and the solution is evaporated to dryness. The oily residue is dissolved without recrystallization in tetrahydrofuran and reduced as described in Example 3, Step (c). The excess of the reducing agent is decomposed by adding ethanol, the mixture is evaporated to about the one-third of its volume, the residue is taken up in 200 ml of 20% potassium sodium tartrate solution and the product is extracted into ethyl acetate. The organic phase is washed to neutral by using aqueous sodium chloride solution, then dried and evaporated. The thus-obtained crystalline residue 5.0 g is washed with diisopropyl ether on the filter to give 4.61 g of the aimed product, m.p.: 168°–170° C. which is identical to the mixture of isomers prepared as described in Example 3, Step (c).

The product of this above Example can be converted e.g. in the following way to the known deoxycorticosterone or its acetate having a mineralocorticoid effect.

Step (a)

Preparation of 21-benzoyloxy-4-pregnene-3,20-dione-3-ethylenedithioacetal

A suspension containing 9.6 g (18.8 mmoles) of 20-benzoylamino-21-hydroxy-4,17-pregnadiene-3-one-ethylenedithioacetal in 160 ml of 90% acetic acid is refluxed for 2 hours, then cooled and poured to 2 liters of 10% ice-cold aqueous sodium chloride solution while stirring. The precipitate is filtered, washed with water and dried to give 6.96 g (72% yield) of the aimed product, m.p.: 179°–181° C. (after recrystallization from ethyl acetate).

Step (b)

Preparation of 4-pregnene-3,20-dione-21-ol benzoate deoxycorticosterone benzoate A suspension of 6.60 g (12.92 mmoles) of 21-benzoyloxy-4-pregnene-3,20-dione-3-ethylenedithioacetal in 40 ml of tetrahydrofuran is added to a suspension containing 5.6 g of red mercury oxide and 3.3 ml of boron trifluoride diethyl etherate in 31 ml of 85% aqueous tetrahydrofuran under vigorous stirring at room temperature. After stirring for 20 minutes, the reaction mixture is mixed with 400 ml of dichloromethane and then filtered. The filtrate is washed successively with a 10% aqueous potassium carbonate solution, then with saturated aqueous sodium chloride solution, dried and evaporated to give 4.76 g of a crystalline residue. This product is subjected to chromatography on a silica gel column by using an 8:1:1 mixture of benzene/ethyl acetate/acetone as eluant to give 4.24 g (76% yield) of the aimed product, m.p.: 205°–207° C.

Step (c)

Preparation of 4-pregnene-3,20-dione-21-ol (deoxycortiocosterone)

A solution containing 7.5 g of potassium hydrogen carbonate in 14 ml of water is added to the suspension containing 2.5 g (5.7 mmoles) of 4-pregnene-3,20-dione-21-ol benzoate in 100 ml of methanol and the mixture is refluxed for 3 hours. Subsequently, the solvent is evaporated and the residue is taken up in 150 ml of water. The product is extracted 3 times with 80 ml of ethyl acetate each, the organic phase is washed with water, dried and evaporated. The residue is recrystallized from a mixture of ethyl acetate and diisopropyl ether to give 1.89 g 99% yield of the aimed product, m.p.: 132°–135° C., $[\alpha]_D = +175.2°$ (c=0.5 in ethanol).

Step (d)

Preparation of 4-pregnene-3,20-dione-21-ol acetate (deoxycorticosterone acetate)

1.16 g (3.5 mmoles) of 4-pregnene-3,20-dione-21-ol [prepared as described in Step (c) above] are acetylated as described in Example 2 to give 1.16 g (89% yield) of the aimed product, m.p.: 156°–158° C., $[\alpha]_D = +174°$ (c=1.0 in dioxane).

EXAMPLE 5

Preparation of 20-benzoylamino-21-acetoxy-4,17-pregnadiene-3-one-ethylenedithioacetal 6.58 g of 20-benzoylamino-21-hydroxy-4,17-pregnadiene-3-one-ethylenedithioacetal (prepared as described in Example 4) are acetylated as described in Example 2 to give 6.35 g (89% yield) of the aimed product, m.p.: 101° C.

EXAMPLE 6

Preparation of 20-benzoylamino-21-acetoxy-4,7-pregnadiene-3-one

A suspension of 2.45 g of 20-benzoylamino-21-acetoxy-4,17-pregnadiene-3-one-ethylenedithioacetal (prepared as described in Example 5) in 8.9 ml of tetrahydrofuran is added dropwise to a suspension containing 1.94 g of red mercury oxide and 1.12 ml of boron trifluoride diethyl etherate in 11 ml of 85% aqueous tetrahydrofuran at room temperature under vigorous stirring. After 30 minutes, 40 ml of dichloromethane are added to the reaction mixture while stirring, then the mixture is filtered through Hyflo Super Cel (Fluka) filter aid. The filtrate is washed first with 10% aqueous potassium carbonate solution, then the aqueous sodium chloride solution, dried and evaporated to give 1.60 g (m.p.: 101°–103° C.) of a crystalline residue. This product is subjected to chromatography on a silica gel column by using a 3:1 mixture of chloroform and ethyl acetate as eluant. The mixture of isomers is collected as a single fraction having an $R_f$ value of about 0.35. 1.25 g of the aimed product are obtained, m.p.: 107°–110° C.

IR (KBr): 3300 cm$^{-1}$ (NH), 1730 cm$^{-1}$ (acetyl), 1660 (CO+amide I).

$^1$H-NMR (CDCl$_3$): 1.08 and 0.97 (2 x s, 3H, H-18); 1.15 (s, 3H, H-19); 2.02 and 2.00 (2 x s, 3H, Ac); 4.83 and 4.60 (2 x s, 2H, CH$_2$O); 5.66 (s, 1H, H-4); 7.25 (b, 1H, NH).

EXAMPLE 7

Preparation of 20-benzoylamino-21-hydroxy-4,9,17-pregnatriene-3-one-ethylenedithioacetal

Step (a)

Preparation of 4,9-androstadiene-3,17-dione-3-ethylenedithioacetal 13.8 g of 4.9-androstadiene-3,17-dione are dissolved in a mixture containing 12.4 ml of 1,2-ethanedithiol and 550 ml of methanol under heating, then the solution is cooled to 25° C. and 12 ml of boron trifluoride diethyl etherate are added while stirring. The temperature of the reaction mixture is kept at 25° C. by a mild cooling. Precipitation of a crystalline substance is observed after a few minutes. After stirring for 15 minutes at room temperature, the suspension is cooled by an ice-water bath, the precipitated product is filtered by suction after 1 hour and washed with a little amount of methanol. The thus-obtained product (13.25 g) is recrystallized from ethanol to give 11.5 g of the aimed product, m.p.: 179°–180° C., [α]$_D$= +233.6° (c=1 in chloroform).

Step (b)

Preparation of 17-(2'-phenyl-5'-oxo-2'-oxazoline-4'-ylidene)-4,9-androstadiene-3-one ethylenedithioacetal The process described in Example 3, Step (a) is followed by using 3.27 g (9 mmoles) of 4,9-androstadiene-3,17-dione-3-ethylenedithioacetal [prepared as described in Step (a) above] as starting material. The crude product is subjected to chromatography on a silica gel column by using a 96:4 mixture of benzene and acetone as eluant to give 3.58 g (78% yield) of the aimed product with an $R_f$ value of about 0.8 to 0.9 as a mixture of two isomers, m.p.: 178°–179° C.

IR (KBr): 1790 cm$^{-1}$ (CO, ring, 1650 cm$^{-1}$ (C=N).

$^1$H-NMR (CDCl$_3$): 1.03 (s, 3H, H-18); 1.20 (s, 3H, H-19); 5.45 (m, 2H, H-4, 11).

Step (c)

Preparation of methyl 20-benzoylamino-4,9,17-pregnatriene-3-one-ethylenedithioacetal-21-oate The process described in Example 3, Step (b) is followed by using 4.54 g (9 mmoles) of 17-(2'-phenyl-5'-oxo-2'-oxazoline-4'-ylidene)-4,9-androstadiene-3-one-ethylenedithioacetal [prepared as described in the preceding Step (b)] as starting material to give 4.38 g (91% yield) of the aimed product as a mixture of two isomers.

This mixture can be separated on a silica gel column by using a 9:1 mixture of benzene and acetone as eluant to give the one isomer with an $R_f$ value of about 0.75, m.p.: 127° C., and the other isomer with an $R_f$ value of 0.50, m.p.: 170° C. On reacrystallization the crude product from ethyl acetate, the more polar isomer can be obtained in a pure form.

IR (KBr): 3410 cm$^{-1}$ (NH), 1720 cm$^{-1}$ (CO), 1660 cm$^{-1}$ amide I).

$^1$H-NMR (CDCl$_3$)(for the isomer with an $R_f$ value of 0.75): 1.07 (s, 3H, H-18), 1.17 (s, 3H, H-19); 3.73 (s, 3H, OCH$_3$); 5.36 (m, 1H, H-11); 5.45 (s, 1H, H-4).

$^1$H-NMR (DMSO-d$_6$) (for the isomer with an $R_f$ value of 0.50): 0.87 (s, 3H, H-18), 1.10 (s, 3H, H-19); 3.57 (s, 3H, OCH$_3$); 5.23 (m, 1H, H-11); 5.33 (s, 1H, H-4).

Step (d)

Preparation of 20-benzoylamino-21-hydroxy-4,9,17-pregnatriene-3-one-ethylenedithioacetal 1.0 g of methyl 20-benzoylamino-4,9,17-pregnatriene-3-one-ethylenedithioacetal-21-oate [the more polar isomer with an $R_f$ value of 0.50, prepared as described in the preceding Step (c)] is reduced as described in Example 1, Step (c) to give 0.88 g (93% yield) of the aimed product containing one individual stereoisomer, m.p.: 212°–213° C. after recrystallization from methanol.

IR (KBr): 3350 cm$^{-1}$ (OH), 3200 (NH), 1640 (amide I).

$^1$H-NMR (CDCl$_3$): 0.87 (s, 3H, H-18); 1.15 (s, 3H, H-19); 4.16 (s, 2H, OCH$_2$); 5.30 (m, 1H, H-11); 5.43 (s, 1H, H-4).

4,9-Androstadiene-3,17-dione used as starting material for this Example can be prepared e.g. in the following way.

15.26 g (50.46 mmoles) of 9α-hydroxyandrost-4-ene-3,17-dione are added portionwise within 20 minutes, under stirring to 40 to 45 g of polyphosphoric acid kept at a temperature of 40° to 45° C., then the mixture is stirred at the same temperature for 2 hours. Subsequently, the mixture is decomposed by adding 1 liter of ice-water, the precipitate is filtered, washed to neutral with water and dried to constant weight in the air to give 14.13 g (98.46% yield) of the aimed product, m.p.: 199°–201° C.

The product of Example 7 can be converted e.g. in the following way to the known 9(11)-anhydrocorticosterone or to its acetate, respectively, the biological activity of which being similar to that of deoxycorticosterone acetate [R. Casanova et al.: J. Chem. Soc. 1953, 2983].

Step (1)

Preparation of 21-benzoyloxy-4,9(11)-pregnadiene-3,20-dione-3-ethylenedithioacetal The process described for the preparation of 5-pregnene-3,21-diol-20-diol-20-one 21-benzoate (see the further-conversion of the product described in Example 1) is followed by using 3.64 g (7.2 mmoles) of 20-benzoylamino-21-hydroxy-4,9(11),17-pregnatriene-3-one-3-ethylenedithioacetal as starting material, except that the crude product is subjected to chromatography on a silica gel column by using a 3:1 mixture of chloroform and ethyl acetate as eluant to give 2.08 g 57% yield of the aimed product, m.p.: 201°–203° C. after recrystallization from ethyl acetate, $[\alpha]_D = +194.5°$ (c=0.5 in chloroform).

Step (2)

Preparation of 4,9(11)-pregnadiene-3,20-dione-21-ol benzoate

The process described for the preparation of 4-pregnene-3,20-dione-21-ol benzoate (see the further-conversion of the product described in Example 4) is followed by using 4.97 g (9.7 mmoles) of 21-benzoyloxy-4,9(11)-pregnadiene-3,20-dione-3-ethylenedithioacetal as starting material [prepared as described in the preceding Step (a)], except that the crude product is not subjected to chromatography, but it is recrystallized from ethyl acetate under purifying with activated carbon to give 1.8 g (42% yield) of the aimed product, m.p.: 176°–177° C., $[\alpha]_D = +175.1°$ (c=1 in chloroform).

Step (3)

Preparation of 4.9(11)-pregnadiene-3,20-dione-21-ol

The process described for the preparation of 5-pregnene-3β,21-diol-20-one (see the further-conversion of the product described in Example 1) is followed by using 1.0 g (2.2 mmoles) of 4,9(11)-pregnadiene-3,20-dione-21-ol benzoate [prepared as described in the preceding Step (b)], except that the crude product is subjected to chromatography on a silica gel column by using a 3:1 mixture of chloroform and ethyl acetate as eluant to give 0.65 g (89% yield) of the aimed product, m.p.: 147°–150° C.

EXAMPLE 8

Preparation of 20-benzoylamino-21-hydroxy-4,9,17-pregnatriene-3-one-ethylenedithioacetal The process described in Example 4 is followed by using 4.38 g (8.18 mmoles) of 17-(2′-phenyl-5′-oxo-2′-oxazoline-4′-ylidene)-4,9-androstadiene-3-one-ethylenedithioacetal [prepared as described in Example 7, Step (b)]. The crude product (4.7 g) is isolated as an oily residue which becomes crystalline by treating with diisopropyl ether to give 3.95 g (95% yield) of the aimed product as a mixture of two stereoisomers, m.p.: 189°–191° C.

EXAMPLE 9

Preparation of 20-benzoylamino-21-acetoxy-4,9,17-pregnatriene-3-one-ethylenedithioacetal 2.5 g of 20-benzoylamino-21-hydroxy-4,9,17-pregnatriene-3-one-ethylenedithioacetal (prepared as described in Example 8) are acetylated as described in Example 5 to give 2.34 g (86% yield) of the aimed product, m.p.: 195°–197° C.

EXAMPLE 10

Preparation of 20-benzoylamino-21-acetoxy-4,9,17-pregnatriene-3-one

The process described in Example 6 is followed by using 2.58 g of 20-benzoylamino-21-acetoxy-4,9,17-pregnatriene-3-one-ethylenedithioacetal (prepared as described in Example 9) to give 2.37 g of a crude product which is subjected to chromatography on a silica gel column by using a 8:1:1 mixture of benzene/ethyl acetate/acetone as eluant. The aimed product is isolated as a single fraction with an $R_f$ value of about 0.3 to 0.4 as a mixture of isomers in a yield of 1.47 g, m.p.: 101°–103° C.

IR (KBr): 3320 cm$^{-1}$ (acetyl), 1660 cm$^{-1}$ (CO+amide I).

$^1$H-NMR (CDCl$_3$): 1.00 and 0.93 (2 x s, 3H, H-18); 1.36 and 1.32 (2 x s, 3H, H-19); 2.06 and 2.00 (2 x s, 3H, Ac); 4.90 (2 x d) and 4.76 (s, 2H, CH$_2$O); 5.45 (m, 1H, H-11); 5.70 (s, 1H, H-4); 7.3 (b, 1H, NH).

EXAMPLE 11

Preparation of 3-methoxy-20-benzoylamino-19-nor-pregna-1,3,5(10),17-tetraene-21-ol

Step (a)

Preparation of 3-hydroxy-17-(2′-phenyl-5′-oxo-2′-oxazoline-4′-ylidene)-estra-1,3,5(10)-triene methyl ether The mixture of 6.6 ml (60 mmoles) of titanium tetrachloride with 13 ml of carbon tetrachloride is added dropwise to 40 ml of tetrahydrofuran at a temperature between 0° and 5° C. Then a solution containing 5.68 g (20 mmoles) of estrone methyl ether and 4.0 g (25 mmoles) of 2-phenyl-2-oxazoline-5-one in 110 ml of tetrahydrofuran is added portionwise at the same temperature during 15 minutes, whereupon 10 ml of pyridine are dropped to the reaction mixture at the same temperature within 9 minutes, then the mixture is stirred for additional 3 hours at room temperature and finally it is decomposed by adding 200 ml of ice-cold 10% aqueous sodium chloride solution. The product is extracted into dichloromethane, the organic solution is washed to neutral with water, dried and evaporated to give an oily residue which becomes crystalline by treating with diisopropyl ether. The thus-obtained crude product (7.0 g) is recrystallized firstly from ethyl acetate and then from acetone to give 1.76 g of the aimed product, m.p.: 193°–194° C. On evaporating the mother liquors to dryness and subjecting the residue to chromatography on a silica gel column by using a 96:4 mixture of benzene and acetone as eluant, an additional amount of 3.55 g of the aimed product is obtained with an $R_f$ value of about 0.7 to 0.8, m.p.: 162° C. containing the isomers in a proportion which is different from that in the preceding (above) fraction. The total yield is calculated together for the first and second crop amounts to 62%.

IR (KBr): 1785 cm$^{-1}$ (CO), 1660 cm$^{-1}$ (C=N).

$^1$H-NMR (CDCl$_3$): 1.06 (s, 3H, H-18); 3.73 (s, 3H, OCH$_3$).

Step (b)

Preparation of methyl 3-methoxy-20-benzoylamino-19-nor-pregna-1,3,5(10),17-tetraene-21-oate The process described in Example 1, Step (b) is followed by using 4.28 g of 3-hydroxy-17-(2'-phenyl-5'-oxo-2'-oxazoline-4'-ylidene)-estra-1,3,5(10)-triene methyl ether [prepared as described in the preceding Step (a)] to give 4.38 g (95% yield) of the aimed product as a mixture of isomers, m.p.: 184°–194° C.

IR (KBr): 3300 cm$^{-1}$ (NH); 1720 cm$^{-1}$ (CO), 1650 cm$^{-1}$ (amide I).

$^1$H-NMR (CDCl$_3$): 1.12 and 1.00 (2 x s, 3H, H-18); 3.70 and 3.76 (2 x s, 3H, COOCH$_3$); 3.72 (s, 3H, OCH$_3$).

Step (c)

Preparation of 3-methoxy-20-benzoylamino-19-nor-pregna-1,3,5(10),17-tetraene-21-ol 3.20 g (6.9 mmoles) of methyl 3-methoxy-20-benzoylamino-19-nor-pregna-1,3,5(10),17-tetraene-21-oate [prepared as described in the preceding Step (b)] are reduced as described in Example 1, Step (c). The obtained oily crude product becomes crystalline by treating with methanol to give 2.85 g (95% yield) of the aimed product, m.p.: 164°–166° C.

IR (KBr): 3100–3500 cm$^{-1}$ (OH+NH), 1630 cm$^{-1}$ (amide I).

$^1$H-NMR (CDCl$_3$): 0.95 (s, 3H, H-18); 3.70 (s, 3H, OCH$_3$); 4.16 (s, 2H, OCH$_2$).

EXAMPLE 12

Preparation of 3-methoxy-20-benzoylamino-19-nor-pregna-1,3,5(10),17-tetraene-21-ol acetate 1.3 g of 3-methoxy-20-benzoylamino-19-nor-pregna-1,3,5(10),17-tetraene-21-ol [prepared as described in Example 11, Step (c)] are acetylated as described in Example 2. The oily crude product obtained after evaporation slowly becomes crystalline by treating with petroleum ether (bp.: 40° C.) to give 1.10 g of the aimed product, m.p.: 95°–97° C.

EXAMPLE 13

Preparation of 20-benzoylamino-21-hydroxy-1,4,17-pregnatriene-3-one

Step (a)

Preparation of 17-(2'-phenyl-5'-oxo-2'-oxazolin-4'-ylidene)-1,4,17-pregnatriene-3-one The process described in Example 3, Step (a) is followed by using 2.84 g (10 mmoles) of 1,4-androstadiene-3,17-dione (Hungarian patent specification No. 146,307) as starting material, except that the crude product is subjected to chromatography on a silica gel column by using a 1:1 mixture of benzene and ethyl acetate as eluant. The obtained 3.3 g of crude foamy product becomes crystalline by treating with diisopropyl ether to give 2.39 g (58% of the aimed product, m.p.: 150°–159° C.

IR (KBr): 1772 cm$^{-1}$ (CO, ring) 1660 cm$^{-1}$ (C=N).
$^1$H-NMR (CDCl$_3$): 0.95 (s, 3H, H-18); 1.10 (s, 3H, H-19); 5.43 (s, 1H, H-4).

Step (b)

Preparation of 20-benzoylamino-21-hydroxy-1,4,17-pregnatriene-3-one

The process described in Example 4 is followed by using 2.3 g (5.56 mmoles) of 17-(2'-phenyl-5'-oxo-2'-oxazolin-4'-ylidene)-1,4,17-pregnatriene-3-one [prepared as described in the preceding Step (a)] as starting material. The obtained 2.0 g of crude product becomes crystalline by treating with diisopropyl ether to give 1.85 g (75%) of the aimed product, m.p.: 124°–128° C.

IR (KBr): 3300 cm$^{-1}$ (OH), 3150 cm$^{-1}$ (NH), 1645 cm$^{-1}$ (amide I).

$^1$H-NMR (CDCl$_3$): 1.03 (s, 3H, H-18); 1.20 (s, 3H, H-19); 5.35 (m, 1H, H-11); 7.25 (b, 1H, NH).

EXAMPLE 14

Preparation of 20-benzoylamino-21-hydroxy-1,4,9,17-pregnatetraene-3-one

Step (a)

Preparation of 17-(2'-phenyl-5'-oxo-2'-oxazolin-4'-ylidene)-1,4,9,17-pregnatetraene-3-one The process described in Example 3, Step (a) is followed by using 2.82 g (10 mmoles) of androsta-1,4,9-triene-3,17-dione (published German patent application No. 3,322,120) as starting material to give 1.95 g (47%) of the aimed product, m.p.: 142°–150° C.

IR (KBr): 1772 cm$^{-1}$ (CO, ring), 1647 cm$^{-1}$ (C=N).
$^1$H-NMR (CDCl$_3$): 0.87 (s, 3H, H-18); 0.99 (s, 3H, H-19); 5.35 (m, 2H, H-4, 11).

Step (b)

Preparation of 20-benzoylamino-21-hydroxy-1,4,9,17-pregnatetraene-3-one

The process described in Example 4 is followed by using 1.86 g (4 mmoles) of 17-(2'-phenyl-5'-oxo-2'-oxazolin-4'-ylidene)-1,4,9,17-pregnatetraene-3-one [prepared as described in the preceding Step (a)] as starting material. The thus-obtained crude product (1.5 g ) is recrystallized from the mixture of ethyl acetate and diisopropyl ether to give 1.39 g (80%) of the aimed product, m.p.: 130°–134° C.

IR (KBr): 3300 cm$^{-1}$ (OH), 3150 cm$^{-1}$ (NH), 1645 cm$^{-1}$ (amide I).

$^1$H-NMR (CDCl$_3$): 1.00, 0.93 (2 x s, 3H, H-18); 1.36, 1.32 (2 x s, 3H, H-19); 5.40 (m, 1H, H-11); 7.2 (b, 1H, NH).

We claim:
1. Pregnene derivatives of the formula (I)

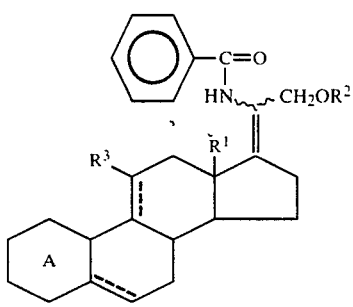

wherein
R$^1$ stands for a C$_{1-4}$ alkyl group;
R$^2$ stands for a hydrogen atom or a C$_{2-4}$ alkanoyl group;
R$^3$ stands for a hydrogen atom, a hydroxyl group or a C$_{2-4}$ alkanoyloxy group, except that R$^3$ is a hydrogen atom when the dotted line between C$_9$ and C$_{11}$ represents an additional valence bond;
A represents a ring of the formula (1)

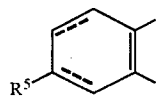

or a ring of the formula (2),

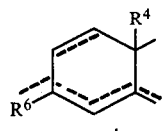

wherein
R$^4$ means a hydrogen atom or a methyl group;
R$^5$ stands for a hydroxy group, a C$_{2-4}$ alkanoyloxy group or a C$_{1-3}$ alkoxy group;
R$^6$ means a hydroxyl group, a C$_{2-4}$ alkanoyloxy group, a C$_{1-3}$ alkoxy group, an oxo group or a C$_{2-3}$ alkylenedithio group; the dotted lines optionally represents one or more additional valence bonds, and the wavy line shows that the given substitutent can be bound to the carbon atom in two alternative spatial arrangements,
as well as their stereoisomers and the mixture of these stereoisomers.

2. A compound selected from the group consisting of
20-benzoylamino-21-hydroxy-4,17-pregnadien-3-one-ethylenedithioacetal,
20-benzoylamino-21-acetoxy-4,17-prenadien-3-one-ethylenedithioacetal,
20-benzoylamino-21-acetoxy-4,17-pregnadien-3-one,
20-benzoylamino-21-hydroxy-4,9,17-pregnatriene-3-one-ethylenedithioacetal,
20-benzoylamino-21-acetoxy-4,9,17-pregnatrien-3-one,
20-benzoylamino-21-hydroxy-1,4,17-pregnatrien-3-one and
20-benzoylamino-21-hydroxy-1,4,9,17-pregnatetraen-3-one.

3. A process for the preparation of the pregnene derivatives of the formula (I)

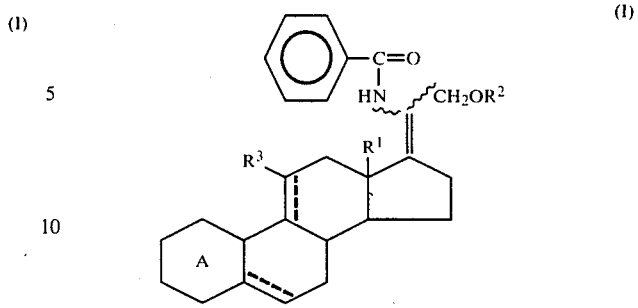

wherein
R$^1$ stands for a C$_{1-4}$ alkyl group;
R$^2$ stands for a hydrogen atom or a C$_{2-4}$ alkanoyl group;
R$^3$ stands for a hydrogen atom, a hydroxyl group or a C$_{2-4}$ alkanoyloxy group, except that R$^3$ is a hydrogen atom when the dotted line beween C$_9$ and C$_{11}$ represents an additional valence bond;
A represents a ring of the formula (1)

or a ring of the formula (2),

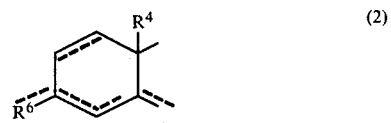

wherein
R$^4$ is a hydrogen atom or a methyl group;
R$^5$ stands for a hydroxyl group, a C$_{2-4}$ alkanoyloxy group or a C$_{1-3}$ alkoxy group;
R$^6$ is a hydroxyl group, a C$_{2-4}$ alkanoyloxy group, a C$_{1-3}$ alkoxy group, an oxo group or a C$_{2-3}$ alkylenedithio group; the dotted lines optionally represents one or more additional valence bonds, and the wavy line shows that the given substitutent can be bound to the carbon atom in two alternative spatial arrangements,
as well as their stereoisomers and the mixture of these stereoisomers, which process comprises:
reducing an alkyl 20-acylamino-pregn-17-ene-21-oate of the formula (V)

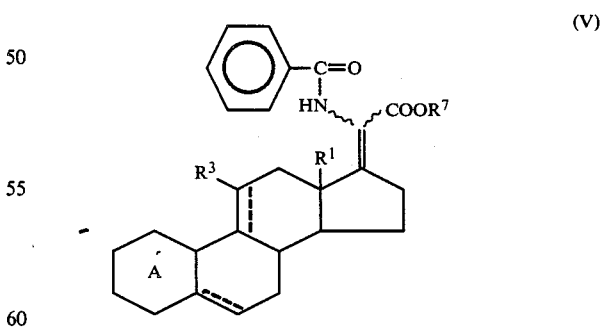

wherein R$^1$, R$^3$, ring A and therein R$^4$, R$^5$ and R$^6$ as well as the meaning of the dotted ans wavy lines are as defined aboe and R$^7$ stands for a C$_{1-3}$ alkyl group with a complex aluminium hydride.

4. The process of claim 3, wherein sodium bis(methoxy-ethoxy)aluminium hydride is used for the reduction of the compounds of the formula (V) to form a pregnene derivative of the formula (I).

UNITED STATES PATENT AND TRADEMARK OFFICE
CERTIFICATE OF CORRECTION

PATENT NO.  : 4,668,437
DATED       : May 26, 1987
INVENTOR(S) : Sandor SOLYOM et al.

It is certified that error appears in the above-identified patent and that said Letters Patent is hereby corrected as shown below:

Column 17, line 41 [hydroxy] should be: hydroxyl

Signed and Sealed this

Seventeenth Day of November, 1987

Attest:

DONALD J. QUIGG

Attesting Officer

Commissioner of Patents and Trademarks